US008529784B2

(12) United States Patent
Cao et al.

(10) Patent No.: US 8,529,784 B2
(45) Date of Patent: Sep. 10, 2013

(54) ELECTRICALLY-CONDUCTIVE AND SEMI-CONDUCTIVE FILMS

(75) Inventors: Tingbing Cao, Beijing (CN); Qiaobing Xu, Somerville, MA (US); Adam Winkleman, Brookline, MA (US); George M. Whitesides, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 752 days.

(21) Appl. No.: 11/989,345

(22) PCT Filed: Aug. 9, 2006

(86) PCT No.: PCT/US2006/031028
§ 371 (c)(1),
(2), (4) Date: Jun. 8, 2009

(87) PCT Pub. No.: WO2007/021741
PCT Pub. Date: Feb. 22, 2007

(65) Prior Publication Data
US 2009/0295364 A1     Dec. 3, 2009

Related U.S. Application Data

(60) Provisional application No. 60/707,073, filed on Aug. 10, 2005, provisional application No. 60/732,325, filed on Nov. 1, 2005.

(51) Int. Cl.
*H01L 29/00* (2006.01)
*H01L 47/00* (2006.01)
*H01L 29/02* (2006.01)
*H01L 29/04* (2006.01)

(52) U.S. Cl.
USPC ............................ 252/1; 252/2; 252/3; 252/4

(58) Field of Classification Search
None
See application file for complete search history.

(56) References Cited

U.S. PATENT DOCUMENTS

| 5,772,905 A | 6/1998 | Chou |
| 6,031,287 A * | 2/2000 | Harshfield ................... 257/734 |

(Continued)

FOREIGN PATENT DOCUMENTS

WO     WO 99/50630     * 10/1999

OTHER PUBLICATIONS

Black, A., et al., "Patterning Disorder in Monolayer Resists for the Fabricatin of Sub-100-nm Structures in Silver, Gold, Silicon and Aluminum," *J. Am. Chem. Soc.*, vol. 121, pp. 8356-8365 (1999).

(Continued)

*Primary Examiner* — Duy Deo
(74) *Attorney, Agent, or Firm* — Wolf, Greenfield & Sacks, P.C.

(57) ABSTRACT

Methods and apparatuses for generating electrically-conductive and/or semi-conductive films, and more specifically, methods and apparatuses for generating conductive and/or semi-conductive films having nanoscale features are provided. In one embodiment, an electrically-conductive or semi-conductive film (e.g., a gold layer of less than 50 nanometer thickness) is provided on a substrate (e.g., a poly (dimethylsiloxane) (PDMS) stamp). The substrate may optionally include patterns or features having raised and recessed portions. A first portion of the film may be removed from the substrate, e.g., by methods such as physically contacting the first portion of the film with a surface to which the first portion preferentially adheres. This process can leave a second portion of the film remaining on the substrate. In some embodiments, the second portion includes at least one region having a dimension substantially parallel to a portion of the substrate i.e., of less than 50 nanometers. The second portion of the film may be used to establish electrical communication with an electrical contact. Advantageously, electrically-conductive and/or semi-conductive films having nanoscale features can be fabricated over large areas (e.g., areas greater than 1 cm²) in a single step.

29 Claims, 5 Drawing Sheets

(56) References Cited

U.S. PATENT DOCUMENTS 6,482,742 B1 11/2002 Chou
7,476,523 B2 * 1/2009 Schueller et al. ............. 435/174

OTHER PUBLICATIONS

Cao, T., et al., "Fabrication of thin, metallic films along th esidewalls of a topographically patterned stamp and their application in charge printing," *Small*, vol. 1, No. 12, pp. 1191-1195 (2005).

Choi, Y., et al., "Fabrication of Sub-10-nm Silicon Nanowire Arrays by Size Reduction Lithography," *J. Phys. Chem.*, vol. 107, pp. 3340-3343 (2003).

Gates, B., et al., "Shear Patterning of Microdominos: A New Class of Procedures for Making Micro- and Nanostructures," *Angew.. Chem.*, vol. 43, pp. 2780-2783 (2004).

Gates., B., et al., "New Approaches to Nanofabrication: Molding, Printing, and Other Techniques," *Chem. Rev.*, vol. 105, pp. 1171-1196 (2005).

Geissler, M., et al., "Defect-Tolerant and Direction Wet-Etch Systems for Using Monolayers as Resists," *Langmuir*, vol. 18, pp. 2374-2377 (2002).

Loo, Y., et al., "Additive, nanoscale patterning of metal films with a stamp and a surface chemistry mediated transfer process: Applications in plastic electronics," *App. Sci.*, vol. 81, No. 3, pp. 562-564 (2002).

Loo, Y., et al., "Interfacial Chemistries for Nanoscale Transfer Printing," *J. Am. Chem. Soc.*, vol. 124, pp. 7654-7655 (2002).

Love, C., et al., "Fabrication of Nanometer-Scale Features by Controlled Isotropic Wet Chemical Etching,"*Adv. Mater.*, vol. 13, No. 8, pp. 604-607 (2001).

McLellan, J., et al., "Edge Spreading Lithography and Its Application to the Fabrication of Mesoscopic Gold and Silver Ring," *J. Am Chem. Soc.*, vol. 126, pp. 10830-10831 (2004).

Melosh, N., et al., "Ultrahigh-Density Nanowire Lattices and Circuits," *Science*, vol. 300, pp. 112-115 (2003).

Menard, E., et al., "Improved Surface Chemistries, Thin Film Deposition Techniques, and Stamp Designs for Nanotransfer Printing," *Langmuir*, vol. 20, pp. 6871-6878 (2004).

Odom, T., et al., "Generation of 30-50 nm Structures Using Easily Fabricated, Composite PDMS Masks," *J. Am. Chem. Soc.*, vol. 124, pp. 12112-12113 (2002).

Whitesides, G., "The Right Size in Nanobiotechnology," *Nature*, vol. 21, No. 10, pp. 1161-1165 (2003).

Xu, Q., et al., "Fabrication of Metal Structures with Nanometer-Scale Lateral Dimensions by Sectioning Using a Microtome," *J. Am Chem. Soc.*, vol. 126, pp. 1332-1333 (2004).

Zaumeseil, et al., "Three-Dimensional and Multilayer Nanostructures Formed by Nanotransfer Printing," *Nano Letters*, vol. 3, No. 9, pp. 1223-1227 (2003).

International Search Report dated Apr. 16, 2007 in PCT/US2006/031028.

Written Opinion dated Apr. 16, 2007 in PCT/US2006/031028.

Austin, Michael D. et al., "Fabrication of a Molecular Self-Assembled Monolayer Diode Using Nanoimprint Lithography" Nano Letters 2003, vol. 3, No. 12, pp. 1687-1690.

* cited by examiner

ELECTRICALLY-CONDUCTIVE AND SEMI-CONDUCTIVE FILMS

RELATED APPLICATIONS

This application is a U.S. National Stage Application of PCT/US2006/031028, filed Aug. 9, 2006, entitled "Electrically-Conductive and Semi-Conductive Films," by Whitesides, et al., which claims the benefit of U.S. Provisional Patent Application Ser. No. 60/707,073, filed Aug. 10, 2005, entitled "Electrically-Conductive and Semi-Conductive Films," by Whitesides, et al., and U.S. Provisional Patent Application Ser. No. 60/732,325, filed Nov. 1, 2005, entitled "Electrically-Conductive and Semi-Conductive Films," by Whitesides, et al., each incorporated herein by reference.

GOVERNMENT FUNDING

This invention was made with government support under DMR-0213805 and PHY-0117795 awarded by the National Institutes of Health, and W911NF-04-1-0170 awarded by the U.S. Army Research Office. The government has certain rights in the invention.

FIELD OF INVENTION

The present invention relates to methods and apparatuses for generating electrically-conductive and/or semi-conductive films, and more specifically, to methods and apparatuses for generating conductive and/or semi-conductive films having nanoscale features.

BACKGROUND

Several methods exist for fabricating micro- and nano-structures, and, particularly, for fabricating electrically-conductive and/or semi-conductive films having micro- and/or nano-scale features. The most commonly used methods for micro- and nanofabrication—photolithography and e-beam writing—have certain limitations: high capital and operating costs, small areas of exposure, and limitations on sizes of features. Many new techniques are being developed to circumvent these current limitations of traditional lithography. A theme common to several of these techniques is size-reduction: that is, using "large and easy to fabricate" masks or templates to yield similarly shaped features that are a fraction of the original size. Size-reduction techniques using variations on photolithography include phase-shifting photolithography, photolithography with undercutting at lithographically defined step-edges, edge lithography with deposition or removal of material in regions defined by defects at the edges of topographic features, and size-reduction photolithography. Edge-spreading lithography, a combination of microcontact printing and controlled chemical diffusion, is a non-photo lithographic technique that also uses mesoscopic templates to generate nanometer features.

While the above-described methods represent significant advances in micro- and nanofabrication, improvements are needed.

SUMMARY OF THE INVENTION

Methods and apparatuses associated with electrically-conductive and/or semi-conductive films are provided.

In one aspect, the invention provides a series of methods. In one embodiment, a method comprises providing an electrically conductive or semi-conductive film of less than 50 nanometer thickness on a substrate, removing a first portion of the film while leaving a second portion of the film on the substrate without the necessity of removing a portion of the substrate, the second portion of the film including at least one region having a dimension substantially parallel to a portion of the substrate of less than 50 nanometers, and establishing electrical communication between the second portion and an electrical contact.

In another embodiment, a method comprises providing an electrically conductive or semi-conductive film on a substrate having raised portions and recessed portions, removing a first portion of the film from a raised portion while leaving a second portion of the film on the substrate, and establishing electrical communication between the second portion and an electrical contact.

In another embodiment, a method comprises providing an electrically conductive or semi-conductive film on a substrate, removing a first portion of the film while leaving a second portion of the film on the substrate, wherein removing comprises physically contacting the first portion of the film with a surface to which the first portion of the film preferentially adheres, and establishing electrical communication between the second portion and an electrical contact.

In another embodiment, a method comprises providing an electrically conductive or semi-conductive film on a conformable substrate, removing a first portion of the film while leaving a second portion of the film on the substrate, and establishing electrical communication between the second portion and an electrical contact.

In another embodiment, the invention provides a series of articles. In one embodiment, an article comprises a conformable substrate including at least one raised portion having a surface contiguous with at least one recessed portion via a sidewall, the sidewall including an electrically-conductive and/or semi-conductive portion having a dimension substantially parallel to the raised portion of the substrate of less than 50 nanometers, wherein the surface of the raised portion is substantially non-electrically conductive and/or non-semi-conductive except for the electrically-conductive and/or semi-conductive portion of the sidewall.

In another embodiment, a sensor system is provided. The sensor system comprises an electrode made by a process according to any preceding claim, a sample region to which the electrode is exposed, and an electrical circuit, in electrical communication with the electrode, constructed and arranged to determine a change in an electrical property associated with the electrode responsive to an interaction of the electrode with a species in the sample region.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
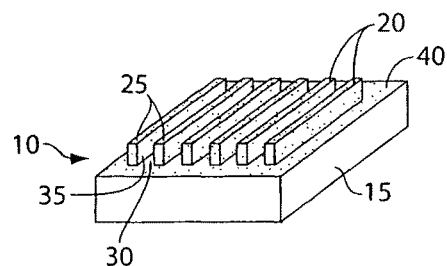
FIG. 1 shows a schematic representation outlining steps involved in fabricating electrically-conductive and/or semi-conductive films according to one embodiment of the invention.

The present invention relates to methods and apparatuses for generating electrically-conductive and/or semi-conductive films, and more specifically, to methods and apparatuses for generating conductive and/or semi-conductive films having nanoscale features. In one embodiment, an electrically-conductive or semi-conductive film (e.g., a gold layer of less than 50 nanometer thickness) is provided on a substrate (e.g., a poly(dimethylsiloxane) (PDMS) stamp). The substrate may optionally include patterns or features having raised and recessed portions. A first portion of the film may be removed from the substrate, e.g., by methods such as physically contacting the first portion of the film with a surface to which the first portion preferentially adheres. This process can leave a second portion of the film remaining on the substrate. In some embodiments, the second portion includes at least one region having a dimension substantially parallel to a portion of the substrate i.e., of less than 50 nanometers. The second portion of the film may be used to establish electrical communication with an electrical contact.

Advantageously, electrically-conductive and/or semi-conductive films having nanoscale features can be fabricated over large areas (e.g., >1 $cm^2$) in a single step. In addition, these films may be formed on flexible substrates in some embodiments.

The methods and apparatuses of the present invention can be used in a variety of settings. One such setting, described in more detail below, involves transferring patterns of charge over large areas. Another setting involves establishing electrical communication through chemical and/or biological substances (e.g., cells).

FIG. 1 is a schematic illustration of a process for fabricating apparatus 10 including electrically-conductive and/or semi-conductive films (e.g., metal films) on a substrate. In the embodiment illustrated in FIG. 1A, substrate 15 includes features 20 comprising raised portions 25, recessed portions 30, and sidewalls 35. A film layer 40 (e.g., gold (Au) and titanium (Ti)) can be deposited on the substrate to cover all or only portions of the substrate.

In some embodiments, a portion of the film on apparatus 10 can be removed. In one particular embodiment, apparatus 10 acts as an article, or "stamp" to transfer material from the substrate (e.g., from raised portions 25) to a second surface by removing a portion of the film from the substrate. In most embodiments of the invention the article, or "stamp", acts to remove material from a surface rather than to transfer material to a surface.

Figure 1B:
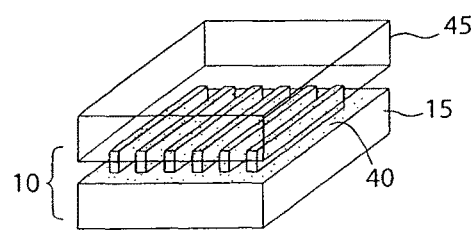

FIG. 1B shows apparatus 10 being brought into contact with second surface 45. The second surface can have appropriate surface chemistry such that contact with apparatus 10 can selectively transfer the film layer from raised portions 25 to the second surface.

In the description herein concerning transfer of material from one surface to another (removal of material from select portions of a surface), those of ordinary skill in the art can select substrates, materials, transferring articles, etc. based upon general knowledge of the art and available reference materials concerning preferential adhesion between certain materials relative to other materials, in combination with the description herein.

Any suitable method can be used to remove a portion of a film from a substrate. Removal may depend on the relative adhesion of the film between the substrate surface and a second surface. For instance, the film may prefer to adhere to a surface that is chemically or physically compatible with the film. Compatibility may be defined by having a relatively low interfacial energy between the film and a surface. For example, if the interfacial energy between a film and a substrate is higher than that between the film and a second surface, the film may be removed from the substrate and may preferentially adhere to the second surface, i.e., when the film and the second surface are brought into contact. A method for film removal may take advantage of factors such as weak adhesion of the film to the original substrate (i.e., the stamp), strong adhesion to the medium (e.g., a substrate or a fluid) to which the film transfers, and/or conformal contact accomplished by the original substrate (i.e., if the original substrate is elastomeric). In some cases, the medium to which the film transfers comprises a high energy surface, e.g., a charged surface. A high energy surface may cause any suitable material (e.g., a film) brought into contact with the surface to adhere to the surface, since it is energetically favorable to lower the surface free energy of a high energy surface.

In one embodiment, a method for removing portion of film includes weakening of the adhesion between the film and substrate, e.g., by bringing the substrate into contact with a fluid which solvates the metal film. In another embodiment, a method for removing film involves the deposition of two or more layers of film of different materials on a substrate. For instance, a first layer of film (e.g., gold) may be deposited on a substrate followed by a second layer of film (e.g., titanium) on top of the first layer. The first layer may have a relatively weak adhesion to the substrate, but may have a strong adhesion to the second layer of film. When the second layer of film is brought into contact with a second surface, the second layer may have relatively stronger adhesion to the second surface than the first layer of film does to the substrate. In other words, the interfacial energy between the second layer of film and the second surface may be relatively lower (i.e., more compatible or energetically favorable) than the interfacial energy between the first layer of film and the substrate. If the strongest adhesion occurs between the first and second layers of film, both layers of film may be transferred from the substrate to the second surface, the first layer now forming the outermost layer of film on the second surface. Relative adhesion and/or interfacial energies between materials are known or may be determined by those of ordinary skill in the art using routine experimentation.

In some cases, removal of a portion of the film can take place without the necessity of removing a portion of the substrate. For instance, in one embodiment, a film portion can be removed without cutting, e.g., with a sharp object such as a razor blade, a portion of the substrate. In other embodiment, a film portion can be removed without etching (i.e., chemically) a portion of the substrate.

Figure 1C:
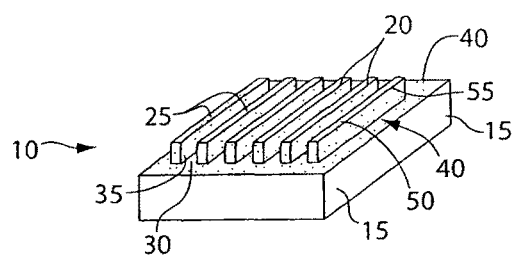

FIG. 1C shows apparatus 10 after the removal of film from raised portions 25 of the features. As illustrated in this embodiment, raised portions 25 show exposed material 50 of the substrate after the removal of portions of film. After the removal of film (e.g., a first portion of film) from the substrate, another portion of film (e.g., a second portion of film) may be left on the substrate. For instance, a film layer may remain on sidewalls 35 and/or recessed portions 30. The portions of the substrate in which a film layer remains after selective removal of film can depend on how the film layer was initially deposited onto the substrate, as discussed in more detail below. In some embodiments, a remaining portion of film on the substrate (e.g., the second portion of film) includes a region having a dimension substantially parallel to a portion of the substrate. For example, if a portion of a substrate is in the form of a straight line, the remaining portion of the film may have at least one region in the form of a straight line; if a portion of the substrate is in the form of a semi-circle, the remaining portion of the film may have at least one region in the form of a semi-circle. A remaining portion of the film may include edges 55 formed between sidewalls 35 and exposed material 50; these edges can be substantially parallel to certain raised portions of the substrate. Sometimes, the remaining portion can have at least one section with a thickness of less than or equal to 100 nanometers, less than or equal to 50 nanometers, less than or equal to 40 nanometers, less than or equal to 30 nanometers, less than or equal to 20 nanometers, or less than or equal to 10 nanometers. In some instances, the remaining portion of film can have at least one section having a thickness between 10-40 nanometers, between 20-40 nanometers, between 30-40 nanometers, between 10-20 nanometers, or between 20-30 nanometers.

Advantageously, the present invention provides methods for fabricating electrically-conductive and/or semi-conductive structures having nanometer features. For instance, the methods can be used to fabricate 10-40 nm-thick, vertically patterned metallic structures rapidly and simply. Methods of the invention can also enable the formation of structures having nanometer features on flexible substrates (e.g., polymers), a process which may be difficult to perform using conventional photolithographic techniques.

Figure 1D:
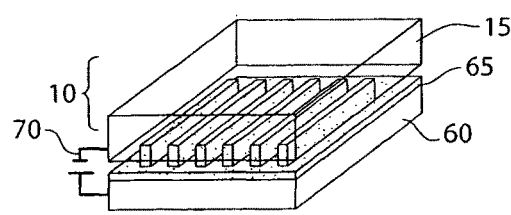
Figure 1E:
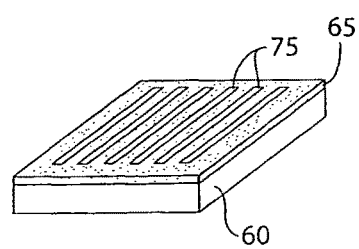

In some embodiments, electrical communication can be established between a remaining portion of film (e.g., the second portion) and an electrical contact. Examples of establishing electrical communication are shown in FIGS. 1D-1E, and in FIG. 4; these methods are discussed in more detail below.

Figure 2:
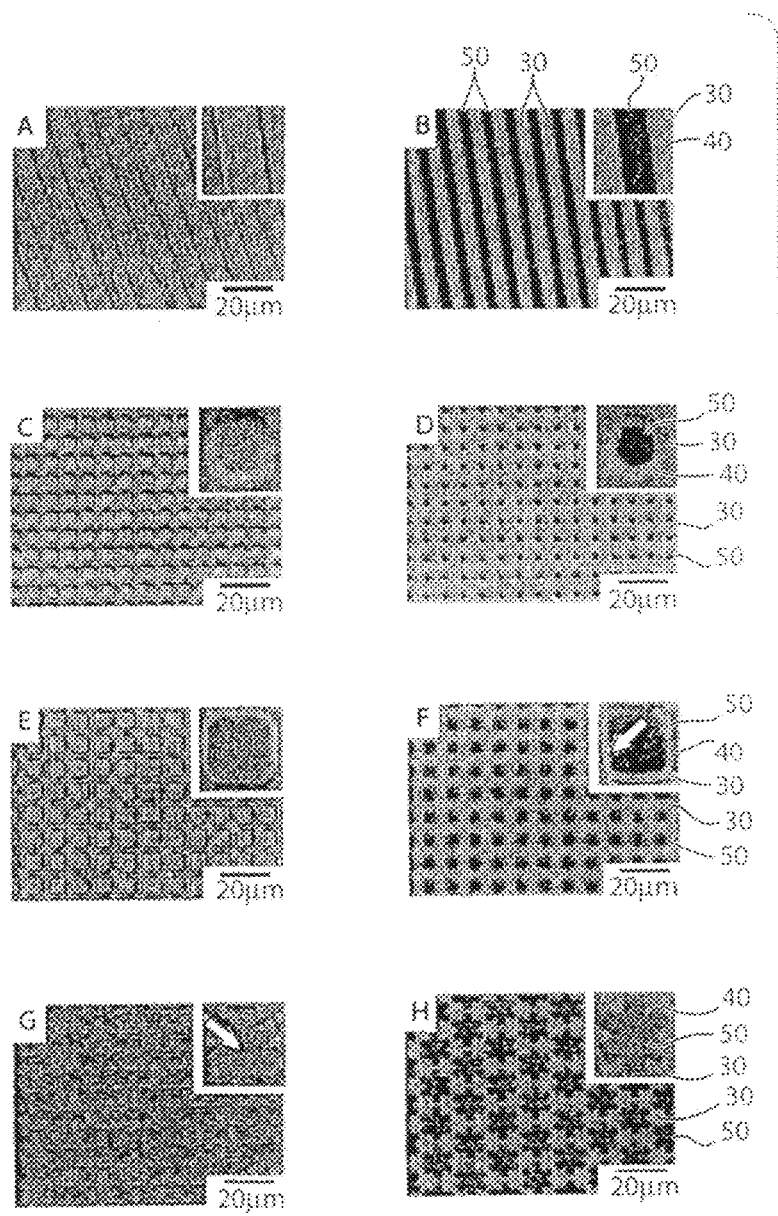
FIGS. 2A-2H show SEM images of metal film-coated substrates before and after removal of portions of film from the substrates according to another embodiment of the invention.
Figure 3A:
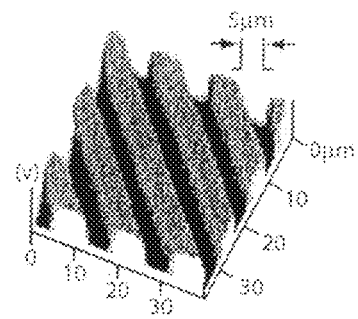
FIGS. 3A-3H show KFM images obtained from electrical micro-contact printing of the metal film-coated substrates illustrated in FIG. 2 according to another embodiment of the invention.
Figure 3B:
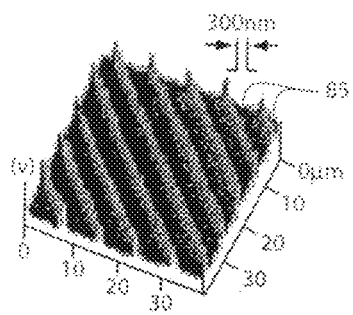
Figure 3C:
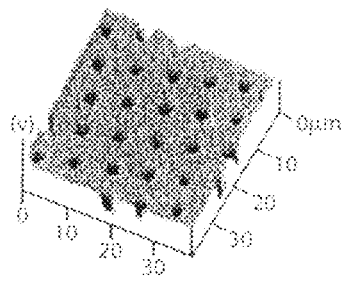
Figure 3D:
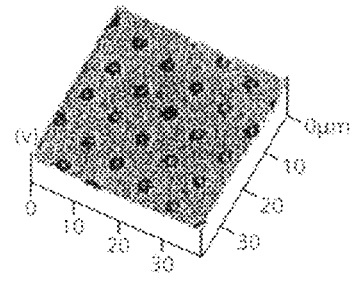
Figure 3E:
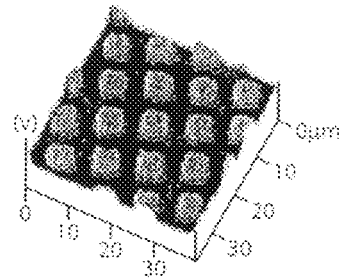
Figure 3F:
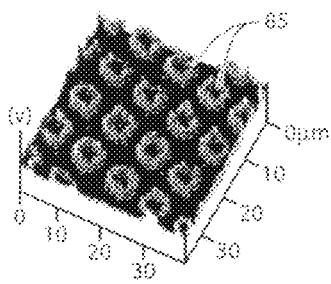
Figure 3G:
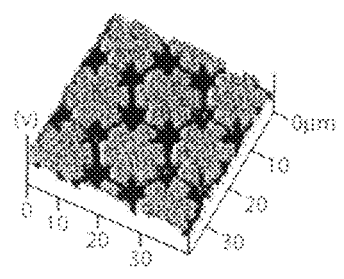
Figure 3H:
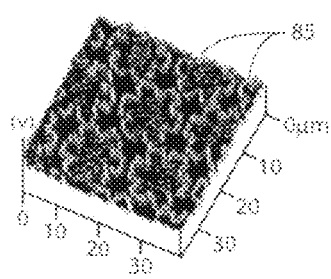

FIG. 2 is a set of scanning electron micrograph (SEM) images of metal film-coated PDMS substrates before (FIGS. 2A, 2C, 2E, and 2G) and after (FIGS. 2B, 2D, 2F, and 2H) removal of a portion of a metal film from the substrates (i.e., via transfer printing). Lines and three types of posts (circular, square, and an asterisk) demonstrated some of the possible patterns of the substrates. Before transfer, metal film was present on all surfaces of the topographically patterned PDMS substrate. After transfer, metal film remained on the sidewalls and recessed portions 30 (i.e., those not brought into conformal contact with the PDMS substrate). In the embodiments illustrated in FIGS. 2A-2H, the thickness of the metal films on the sidewalls of the PDMS ranged from 10-40 nm. The light regions denote metal films 40 and the dark regions denote the exposed regions 50 from the raised lines or posts' tops where the metal was removed. The insets represent an average post and illustrate the quality of the metal film.

Different methods can be used to deposit film 40 on a substrate. Examples of methods for depositing metal films include electroplating, vacuum deposition, and thermal evaporation. Those of ordinary skill in the art are aware of many techniques for depositing electrically-conductive and or semi-conductive films on a substrate.

Films on a substrate can cover all or portions of a substrate. In some instances, a film layer is deposited such that it completely covers the substrate, i.e., the film is a continuous layer; in other instances, a film layer can be discontinuous and discrete regions of film may reside on the substrate. In one embodiment, i.e., as shown in FIG. 1A, non-collimated material deposition can be used to form thin films on all surfaces of the substrate. In another embodiment, collimated material can be deposited substantially normal to the substrate to ensure a discontinuous film; the sidewalls of the features can intentionally be left free of deposited material. In yet another embodiment, material can be deposited at an angle (e.g., less than or equal to 15°, less than or equal to 30°, less than or equal to 45°, less than or equal to 60°, less than or equal to 75°, or less than or equal to 90°) relative to the substrate such that the film is deposited on certain portions of the substrate. The angle of deposition of the film layer may influence the continuity of the film layer, and, therefore, the electrical communication between a film portion and an electrical contact. In some cases, a conductive or semi-conductive material can also be deposited through a mask positioned on top of the substrate in order to obtain a discontinuous film. I.e., openings in the mask can allow material to be deposited onto the substrate, whereas portions of the substrate covered by the mask may be free of deposited material. This method is discussed in more detail below. Advantageously, discrete portions of film on a substrate can be individually addressable by electronic means.

Any suitable conductive and/or semi-conductive material can form a film layer on a substrate according to embodiments of the invention. In one embodiment, all or portions of a film may comprise a metal. In some cases, the metal film includes a transition element. Non-limiting examples of metals include copper (Cu), platinum (Pt), palladium (Pd), gold (Au), nickel (Ni), indium (In), tin (Sn), silver (Ag), lead (Pb), bismuth (Bi), cadmium (Cd), zinc (Zn), antimony (Sb), chromium (Cr), and titanium (Ti). In some embodiments, multiple layers of material can be deposited on a substrate. In one particular embodiment, a layer of gold, for example of about 10-50 nm thickness, is first applied to a substrate, followed by a titanium coating of about 2-5 nm thickness. Of course, conductive and/or semi-conductive coatings are not limited to metals, but may also include other conductive materials such as conductive polymers. In another embodiment, semi-conductive materials such as carbon (C) and silicon (Si) may comprise all or portions of a film.

A layer of film can have varying thicknesses on a substrate. For example, a film may have a thickness of equal to or less than 100 nanometers, equal to or less than 50 nanometers, equal to or less than 40 nanometers, equal to or less than 30 nanometers, equal to or less than 20 nanometers, or equal to or less than 10 nanometers. In some instances, the film can have a thickness between 10-40 nanometers, between 20-40 nanometers, between 30-40 nanometers, between 10-20 nanometers, or between 20-30 nanometers.

A substrate may include a surface having a variety of features defined therein by raised and/or recessed portions. In some instances, the substrate may include features having a variety of lateral dimensions. According to some embodiments of the invention, the substrate may include at least one feature with a lateral dimension of less than 100 microns, less than 50 microns, less than 10 microns, less than 5 microns, less than 1 micron, less than 500 nanometers, less than 250 nanometers, or less than 100 nanometers.

A substrate may include one or several different patterns of features including lines, circles, squares, and irregular shapes. A portion (e.g., a second portion) of a film that remains on a substrate (i.e., after removal of a first portion of film) may include at least one region having a dimension (e.g., a length, width, or thickness) substantially parallel to a portion of the substrate (e.g., the raised portions of the substrate). In some embodiments, the second portion of film forms a perimeter around the raised (or recessed) features. The patterns (e.g., shape, spacing, and numbers) of the films can be controlled by design of the features on the substrate.

In some instances, a substrate is substantially smooth, i.e., the substrate may not include raised and/or recessed portions. The substrate may be planar or curved, and can be conformable in certain embodiments. The substantially smooth substrate may be chemically and/or energetically uniform across the surface. In one embodiment, portions of film can be removed from the substantially smooth surface by bringing the substrate into contact with a second surface that is patterned with raised and/or recessed portions. Portions of film may be transferred from the substrate to the raised regions of the second surface. In another embodiment, the substantially smooth substrate may comprise areas of high energy and low energy to which a film is deposited. Upon contact of the substrate with a second surface, which may also be substantially smooth, portions of film may be removed from the high energy regions of the substrate onto the second surface. Of course, combinations of high/low energy surfaces and raised/recessed portions of surfaces can facilitate removal of portions of film.

A substrate my comprise numerous raised and/or recessed regions. For example, a single substrate may include more than 5000 isolated raised and/or recessed regions, more than $10^6$ isolated raised and/or recessed regions, or more than $10^9$ isolated raised and/or recessed regions. The raised and/or recessed regions may form a "patterning area" on the substrate. In some embodiments, the patterning area is larger than 0.5 cm$^2$, larger than 1 cm$^2$, larger than 2 cm$^2$, or larger than 5 cm$^2$. The patterning area may be defined by the size of the substrate in some cases.

The features included in the raised and/or recessed portions of a surface can be created in a way such that the aspect ratio of any individual feature is greater than 0.2, greater than 0.5, greater than 1.0, greater than 1.5, or greater than 2.0. The aspect ratio is defined as the ratio of minimum lateral dimension of any raised portion of a surface feature to indentation depth. Methods of forming features in a substrate are described in more detail below.

In one embodiment of the invention, a portion of a conductive or semi-conductive film (e.g., a conductive or semi-conductive edge) is used to establish electrical communication with an electrical contact, e.g., in a situation in which the portion of the conductive or semi-conductive film may act as an electrode, and the electrical contact can be electrically connected or otherwise arranged with respect to a circuit enabling use of the electrode for a variety of purposes. In one embodiment, electrical communication is established by placing a dielectric material between a conductive or semi-conductive film and an electrical contact. In one particular embodiment, applying a potential through the layers can cause charges to be embedded in the dielectric material. U.S. Patent Publication No. 2003/0178316 (Jacobs, et al.), which is incorporated herein by reference, describes several arrangements in which the present invention can be employed. Advantageously, conductive or semi-conductive films that are supported by soft substrates (e.g., a polymer or elastomeric polymer such as PDMS) can have good mechanical compliance and can enable good conformal contact with hard dielectric substrates for charge imprinting.

FIGS. 1D-1E illustrate a process for embedding charge from conductive or semi-conductive films (i.e., electrodes) fabricated in FIGS. 1A-1C into dielectric materials. To embed a charge, i.e., into a polymer such as PMMA, apparatus 10 can be brought into contact with material 60 (e.g., silicon) that can include layer 65 of PMMA (FIG. 1D). Potential 70 can be applied between apparatus 10 and material 60. In one embodiment, a current density of ~40 µA/mm$^2$ was passed between the electrodes for 20 seconds. Using this technique, patterns of both positive and negative charge in dielectric materials can be supported on p-doped and n-doped silicon wafers respectively. In the embodiment illustrated in FIG. 1E, areas 75 are regions where the top surfaces of raised portions 25 were in contact with the PMMA surface. Charges can be transferred to the PMMA surfaces along the perimeters of areas 75, i.e., where the film portions of apparatus 10 were in physical contact with the PMMA surface.

FIG. 3 shows Kelvin probe force micrographs of the patterns of embedded charge generated from the corresponding substrates shown in FIG. 2. The images in the left column, FIGS. 3A, 3C, 3E, and 3G, were from substrates completely coated with a thin-metal film and the images in the right column, FIGS. 3B, 3D, 3F, and 3H, were generated by the corresponding substrates after removing the upper plane of metal by transfer printing. In the embodiments illustrated in FIGS. 3B, 3F, and 3H, the widths of lines 85 of electrostatic potential were ~300 nm. In these particular embodiments, the widths did not change over the 10-40 nm range of thicknesses of the metal film. Charges were printed with a single substrate in excess of 150 times without noticing any degradation in the quality of the pattern of charge or in the appearance of the substrate. In some embodiments, metal transfer was seen in the first few cycles of charge printing. This metal is usually from the top flat region of the raised portions of the substrate and not the edge, and reflects incomplete transfer in the step shown in FIG. 1D. It is possible to pattern both positive (FIGS. 3A, 3B, 3E, 3F, 3G, and 3H) and negative (FIGS. 3C and 3D) surface potentials using electrical micro-contact printing (e-µCP).

In the embodiments illustrated in FIG. 3, the substrates used for patterning charge were formed in PMMA. In other embodiments, patterned charges can be formed in other polymeric dielectric materials (including poly(styrene) and Teflon AF™) and in inorganic dielectrics (e.g., SiO$_2$). In one particular embodiment, poly(styrene), Teflon AF™, and SiO$_2$ substrates (all having thicknesses of less than 500 nm) were tested for patterning charge using methods described herein, and yielded similar charge patterns.

Figure 4A:
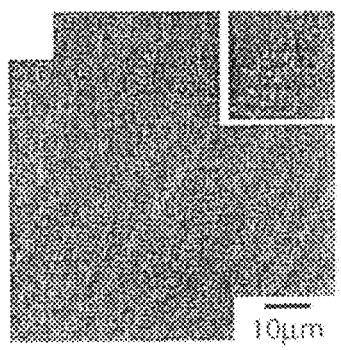
FIGS. 4A-4B show SEM images of nanoparticle adsorption over patterns of charge on positively-charged substrates according to another embodiment of the invention.
Figure 4B:
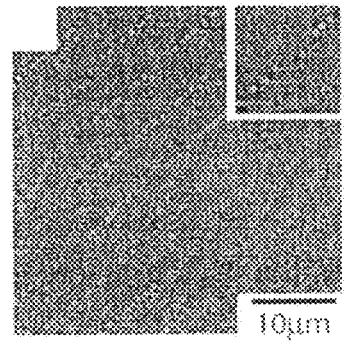
Figure 4C:
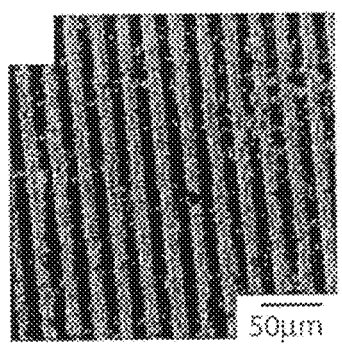
FIGS. 4C-4D show dark field optical images of dry nanoparticles assembled over negatively patterned substrates according to another embodiment of the invention.
Figure 4D:
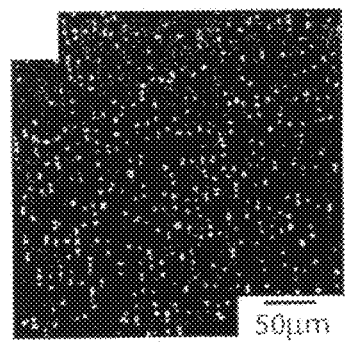

In some embodiments, dielectric surfaces with patterns of charge can be used to adsorb nanoparticles, e.g., nanospheres, selectively. FIGS. 4A and 4B show SEM images of nanoparticle adsorption over the patterns of charge illustrated by the alignment of 200-nm, sulfonate-modified poly(styrene) (PS) spheres over the positively patterned PMMA substrates of FIGS. 3A and 3B. The insets illustrate local particle assembly; the size reduction pattern yields structures having widths of only one particle across. FIGS. 4C and 4D show dark field optical images of dry, neutral iron oxide nanoparticles assembled over a negatively patterned PMMA substrate. FIGS. 4A and 4C are images illustrating the particle assembly and distribution over a pattern of charge using PDMS substrates before metal transfer, and FIGS. 4B and 4D are from substrates patterned with charge from PDMS substrates after metal transfer.

The formation of patterns of nanoparticles, i.e., as illustrated in FIGS. 4A-4D, can be performed by a process such as the following. Using a surface with a pattern of embedded positive charge, the surface can be dipped into an ethanol solution containing nanoparticles, e.g., 200-nm, sulfonate-modified, poly(styrene) spheres. Upon withdrawal from the solution, rinsing the surface with fresh ethanol, and evaporation of the solvent, the nanospheres can selectively adhere to the charged regions. The poly(styrene) spheres have a negative surface potential and were attracted to the regions of positive charge. Using a PMMA film on a p-doped silicon wafer with a pattern of embedded positive charge, the substrate can be dipped into a neutral, dry powder of iron oxide (300-800 nm). Nitrogen gas can be passed over the substrate to remove excess particles. The substrate can also be sonicated in hexane for 3-5 seconds to remove the particles that adhere non-specifically.

According to another embodiment of the invention, a remaining portion of a film (i.e., the second portion of film after a first portion has been removed from a substrate) can be used as an electrode in a chemical and/or biological environment. For instance, electrical communication can be established between an electrode and an electrical contact via a chemical and/or biological component. In some embodiments, a voltage and/or a current can be passed between the electrode and an electrical contact through the chemical and/or biological component in a sample region.

In some embodiments, a cell (e.g., a mammalian or microbial cell) can be positioned between an electrode and an electrical contact. The cell may be positioned directly on top of the electrode, or on top of a non-conductive layer covering the electrode, as discussed in more detail below. Cells are known to respond to electrical impulses and signals. The electrodes (i.e., ones that are fabricated on the sidewalls of raised portions of a substrate using methods described herein) can be easily addressable. For instance, an electrode can be addressable from the edge of the substrate, i.e., via a continuous film of electrically-conductive and/or semi-conductive material. An electrical signal (e.g., AC or DC) can be applied between the electrode and the electrical contact, and the signal can be used to induce responses in the cell over very narrow regions (e.g., several nanometers, the width of the electrode). Cells positioned adjacent the electrodes can experience electric fields from the nanoelectrodes. Methods and apparatus of the present invention can be used, for example, as sensors to study cell behavior (e.g., signal transduction) in a controllable and localized region. Embodiments of the invention can also enable electrical impulses and signals to be directed to many cells in parallel, e.g., by patterning cells over several raised and/or recessed regions of a substrate and applying electrical signals to each of these regions.

In one particular embodiment, a cell can be positioned between two conductive and/or semi-conductive regions on a substrate, and an alternating current (either uniform or non-uniform) can be applied between these regions. The electric fields created by the alternating current can be used to induce cellular responses such as the redistribution of cell surface receptors, cell repulsion from electrode polarization, depolarization of cell membranes, changes in membrane permeability, and changes in conduction of electrical signals in neurons. Embodiments of the invention can also be used to study cell-cell communications (e.g., electrical communication between adjacent neurons) and to probe physical properties of molecules and cells (e.g., the resistance of cell monolayers). In another embodiment, tracer particles (e.g., magnetic particles) may be present on a surface of a cell or inside a cell. These particles, which can be used to study cell surfaces and internal cell structures, can be affected by electrical signals. In some cases, magnetic nanoparticles can react to the magnetic force produced from a current passing through the nanoelectrodes. By tuning the electrical communication between the electrode and electrical contact, these particles can be affected and can be used to stimulate regions of a cell and/or to sense particular activities or components within the cell.

Figure 5A:
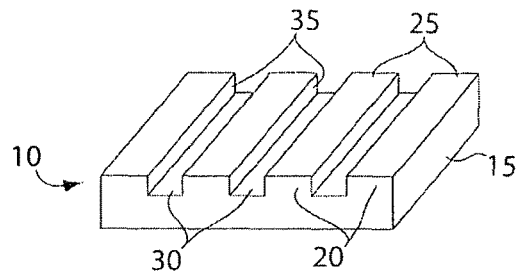
FIG. 5 shows a schematic representation outlining steps involved in fabricating electrically-conductive and or semi-conductive films according to another embodiment of the invention.
Figure 5B:
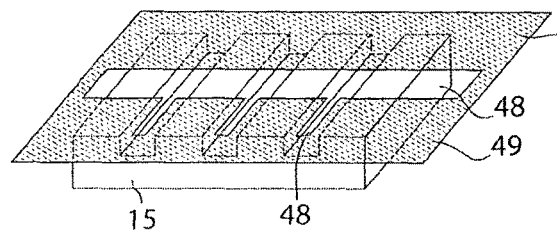
Figure 5C:
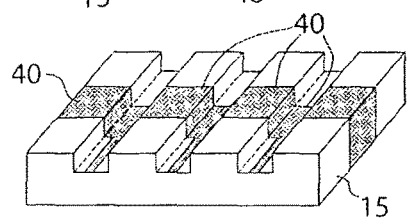
Figure 5D:
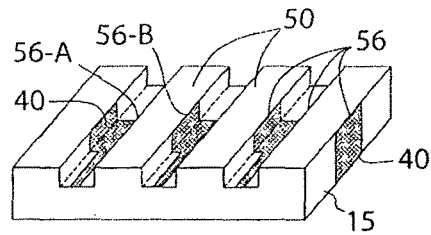

In some embodiments, a conductive or semi-conductive material can be deposited through a mask positioned on top of a substrate. This method can be used to form discontinuous films, as shown in the embodiments illustrated in FIGS. 5A-5F. FIG. 5A shows substrate 15 including features 20 comprising raised portions 25, recessed portions 30, and sidewalls 35. Mask 47, which includes opened region 48 and closed region 49, can be placed proximate substrate 15 (FIG. 5B). Film layer 40, comprising a conductive or semi-conductive material, can be deposited onto the substrate to cover portions of the substrate exposed to the opened regions of the mask (FIG. 5C). If desired, more than one layer of film can be deposited through the mask to form a multi-layered film. Portions of the film can be removed from the substrate of FIG. 5C using various methods described above to obtain the embodiment shown in FIG. 5D. FIG. 5D includes exposed regions 50 (e.g., regions where portions of film have been removed) and conductive or semi-conductive edges 56.

Discrete regions of different conductive or semi-conductive materials can be patterned on a single substrate by repeating the steps shown in FIGS. 5B-5D. Patterning of different films of material can be performed using the same mask (i.e., by re-orienting the mask on the substrate), or by using a mask having a different pattern. A substrate having films of different material may be fabricated when, for example, it is desirable to have discrete regions having different electrical properties on a single substrate.

Figure 5E:
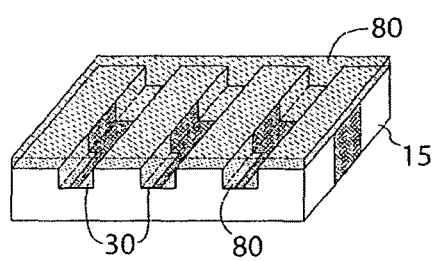

In certain embodiments, one or more layers of non-conductive material can be formed over a substrate after a portion of electrically-conductive or semi-conductive film has been removed from the substrate. For instance, as shown in FIG. 5E, non-conductive layer of material 80 may be formed over substrate 15, e.g., by spin-coating or thermally evaporating the material thereon. FIG. 5E shows non-conductive layer 80 covering the substrate and filling recessed portions 30 of the substrate. In other embodiments, however, one or more layers formed over the substrate may cover the substrate incompletely. For example, in one embodiment, only the top portions of raised portions 25 may be covered with the non-conductive material.

Figure 5F:
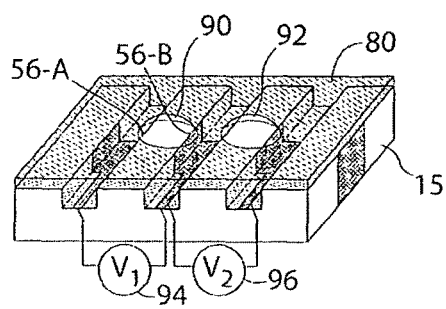

Filling the recessed portions with a non-conductive material may be useful for forming substantially flat substrates having embedded electrical films (i.e., electrodes) therein. Such embodiments can be used as heating elements (e.g., for substrates in microfluidic applications), or as substrates for depositing cells, for example. In some cases, electrical communication can be established between an electrode and an electrical contact through an object (e.g., a chemical and/or biological component) positioned proximate the non-conductive layer. For instance, as illustrated in FIG. 5F, cells 90 and 92 can be positioned proximate non-conductive layer 80 over conductive or semi-conductive edges 56, which can function as electrodes. Electrical communication can be established between an electrode and an electrical contact; for example, as shown in FIG. 5F, a voltage and/or current can be applied between edges 56-A and 56-B via cell 90. In this embodiment, the electrical signal also passes through non-conductive layer 80. Those of ordinary skill in the art can readily control the amount of electrical communication through non-conductive layer 80, e.g., by choosing the material in which non-conductive layer 80 is made and the thickness of the layer.

In some cases, embodiments of the invention can be used in microfluidic applications. For example, in one embodiment, one or more microfluidic channels can be formed in a substrate and a conductive or semi-conductive film can be deposited onto the surface of the substrate (i.e., the surface containing the channels). Alternatively, a mask may be positioned on top of the substrate prior to depositing the conductive or semi-conductive film. A first portion of the film can be removed from the substrate (e.g., by transferring the first portions onto another surface), leaving a second portion of film on the substrate. The second portion of film may reside, for instance, in the trough of the channel. If a mask was used to cover portions of the channel, discrete portions of film may be patterned in the channel. In some embodiments, discrete portions of film can be used to establish electrical communication in a microfluidic channel (i.e., for applications such as electrophoresis) and these discrete portions may be individually addressable if desired. In other embodiments, discrete portions of film in a microfluidic channel can be used to pattern chemical compounds (e.g., to form self-assembled monolayers), which can be used in applications such as chemical and/or biological assays.

In some embodiments, it is advantageous to form electrically-conductive and/or semi-conductive films on flexible (i.e., soft) substrates. For instance, conductive films on flexible substrates can be used as flexible circuit assemblies. A variety of different materials may be suitable for use as substrates for electrically-conductive and/or semi-conductive films. According to one embodiment, a substrate is formed from a polymeric material. Polymeric materials suitable for use in fabrication of the substrate may have linear or branched backbones, and may have a high or low degree of crosslinking (or, alternatively, may be non-crosslinked), depending upon the particular polymer and the degree of formability desired of the substrate. A variety of polymeric materials are suitable for such fabrication, especially polymers of the general classes of silicone polymers, epoxy polymers, and acrylate polymers. Epoxy polymers are characterized by the presence of a three-member cyclic ether group commonly referred to as an epoxy group, 1,2-epoxide, or oxirane. For example, diglycidyl ethers of bisphenol A may be used, in addition to compounds based on aromatic amine, triazine, and cycloaliphatic backbones. Another example includes the well-known Novolac polymers. In some embodiments, additives (e.g., hardening agents) may be added to a polymer in order to achieve a desired property (e.g., formability, hardness, adhesiveness, etc.) of the substrate. In other embodiments, all or portions of a substrate may be treated chemically or with charged species (e.g., by oxidation) to obtain certain properties. Selective regions on a substrate can be treated by applying a mask (i.e., a layer or a sheet having opened and closed portions) over the substrate before treatment. Any suitable mask can be used, including ones that are formed in polymers that conform to the surface to which it contacts.

Examples of silicone elastomers suitable for use as a substrate include those formed from precursors including the chlorosilanes such as methylchlorosilanes, ethylchlorosilanes, and phenylchlorosilanes, and the like. A particularly preferred silicone elastomer is poly(dimethylsiloxane). Exemplary poly(dimethylsiloxane) polymers include those sold under the trademark Sylgard by the Dow Chemical Company, Midland Mich., and particularly Sylgard 182, Sylgard 184, and Sylgard 186.

Non-flexible substrates may also be used as substrates for electrically-conductive and/or semi-conductive films. For example, substrates comprising oxides layers (e.g., silicon oxide) may be suitable in some embodiments.

In another embodiment, the substrate material itself may be conductive or partially-conductive. For example, an elastomeric compound containing conductive materials dispersed therein, such as carbon particles, may be used.

Features of a substrate (i.e., a "mold surface") may be formed according to a variety of methods. According to one method, the mold surface is micromachined from a material such as a semi-conductor. According to another method, the mold surface is formed lithographically by providing a substrate, depositing a film of material onto the substrate, coating an exposed surface of the material with resist, irradiating the resist according to a predetermined pattern, removing irradiated portions of the resist from the material surface, contacting the material surface with a reactant selected to react chemically therewith and selected to be chemically inert with respect to the resist such that portions of the material according to the predetermined pattern are degraded, removing the degraded portions, and removing the resist to uncover portions of the material formed according to the predetermined pattern to form the mold surface. Negative or positive resist may be used, and the procedure adjusted accordingly. According to another method of forming a mold surface, a substrate may be provided, and coated with resist. Then portions of the resist may be irradiated according to a particular predetermined pattern. Irradiated portions of the resist may then be removed from the substrate to expose portions of the substrate surface according to the predetermined pattern, and the substrate may be contacted with a plating reagent such that exposed portions according to the predetermined pattern are plated. Then, the resist may be removed to uncover portions of the exposed substrate according to the predetermined pattern bordered by plated portions of the substrate to form the mold surface.

A substrate according to one embodiment of the present invention may be fabricated as follows. A template consisting of an exposed and developed photoresist pattern on silicon is prepared (this type of fabrication is described in many conventional photolithography texts, such as *Introduction to Microelectronic Fabrication*, by Richard C. Jaeger, Gerold W. Neudeck and Robert F. Pierret, eds., Addison-Wesley, 1989). Templates such as electron microscopy grids or other corrugated materials may also be used. The template is placed in a container such as a petri dish. A 10:1 (w:w or v:v) mixture of PDMS-Sylgard Silicone Elastomer 184 and Sylgard Curing Agent 184 (Dow Corning Corp., Midland, Mich.) is poured into the petri dish. It is not necessary to put the mixture of PDMS-elastomer and curing agent under vacuum to remove dissolved dioxygen. The PDMS is cured at room temperature in the laboratory ambient for 30 to 60 min. This cure is followed by additional curing at 65° C. for approximately one hour or until the polymer is rigid. After cooling to room temperature, the PDMS is carefully peeled from the template and can be used as a substrate.

Advantageously, multiple substrates can be formed from a single template (or mold). Once the substrates are formed, electrically-conductive and/or semi-conductive films can be deposited on the substrates, i.e., simultaneously, and portions of the metal films can be removed from these substrates. This method can allow the simple and rapid fabrication of thin electrically-conductive and/or semi-conductive portions (e.g., having dimensions less than 50 nanometers) on multiple substrates.

A portion (e.g., a first portion) of a conductive and/or semi-conductive film can be transferred to a variety of different surfaces (e.g., a second surface). A surface to which a portion of film is transferred can be made of the same or a different material as that of the substrate. For instance, one or a combination of the materials listed above which are suitable materials for substrates can be used in forming the second surface, or, in other cases, different materials may be used. (In the case of the substrate and the second surface being made in the same material, an addition treatment step to either the substrate or the second surface may be required in order to weaken/strengthen the adhesion of the portion of film on one surface relative to the other. Oxidizing the second surface is one example of a treatment step.) The choice of materials for the second surface may depend on the material of the substrate, material of the film, relative adhesions of the film on both the substrate and the surface, etc. Portions of film may be transferred to either flexible or non-flexible surfaces. The following examples are intended to illustrate certain embodiments of the present invention, but are not to be construed as limiting and do not exemplify the full scope of the invention.

Example 1

This example shows the fabrication of the metal portions on the sidewalls of a substrate according to one embodiment of the invention. Soft lithography and rapid prototyping were used to fabricate features in SU-8 (MicroChem Corp.) that were subsequently replica molded using PDMS pre-polymer to fabricate the flexible substrates (i.e., stamps) having an area greater than 1 cm$^2$. The substrates were coated with 10-40 nm of Au and 2-5 nm of Ti using an electron beam evaporator. The Ti layer promoted adhesion during transfer of the film. These metal film-coated substrates and a flat slab of PDMS were oxidized using an air plasma (~2 torr, 100 W, Harrick Scientific Model PDC-32G) for 1 minute. To transfer the metal film from the raised features, the PDMS substrate and slab were brought into conformal contact and separated. During the separation, the Au/Ti thin-films on the raised portions of the features were transferred to the oxidized PDMS slab. The metal film on the sidewalls of the features and on the recessed portions remained on the PDMS substrate. The metal edge along the sidewalls was thin (i.e., the thickness of the evaporated film: that is, 10 to 40 nm) and sharp, and the entire metal structure remained conductive. The images of the substrates before and after transfer as shown in FIG. 2 were obtained by SEM (LEO 982). This example illustrates a rapid and simple method of fabricating 10-40 nm electrically-conductive features over large areas on a substrate according to one embodiment of the invention. This example also shows that a variety of patterns having 10-40 nm electrically-conductive features can be fabricated.

Example 2

This example shows the use of the electrically-conductive features to print charges on a substrate according to one embodiment of the invention. A thin film of polymer (typically PMMA, 100 nm thick) was spin-coated onto a silicon wafer (Universitywafer.com). This dielectric was brought into conformal contact with the PDMS substrate formed using the methods described in Example 1. An electrical current density of (~40 µA/mm$^2$) was passed for 20 seconds using a Keithley 2400 electrometer. The images of charge as shown in FIG. 3 were obtained using an AFM (D3100, NSIV; Digital Instruments) in surface potential mode. This example shows that 10-40 nm electrically-conductive features can be used to transfer negative and/or positive charges to a substrate to generate nm-scale patterns of charge according to one embodiment of the invention. This example also shows the patterning of charges over large areas (i.e., areas greater than 1 cm$^2$).

Example 3

This example shows that patterns of charge on a substrate can be used to attract nm-scale particles. A solution of 1.7% by weight 200-nm sulfonate-modified polystyrene spheres (Duke Scientific Corporation) in water, 1 mL, was diluted in 10 mL of ethanol. A charged wafer formed by the methods described in Example 2 was placed into the solution for 1 minute. Upon removal from the solution, the substrate was rinsed with fresh ethanol and the substrate was dried using a stream of nitrogen gas. Images, as shown in FIGS. 4A and 4B, were obtained using an SEM (LEO 982).

A positively charged wafer formed by the methods described in Example 2 was dipped into dry, neutral iron oxide particles (300-800 nm, Polysciences, Inc.). A stream of nitrogen gas blew off the excess particles. The substrate was sonicated for 3-5 seconds in a solution of hexanes. Images, as shown in FIGS. 4C and 4D, were obtained using an optical microscope (Leica) in dark field mode. This example shows that 10-40 nm electrically-conductive features can be used to selectively pattern nanoparticles on a substrate over large areas according one embodiment of the invention.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article comprising:
a conformable, polymeric substrate including at least one raised portion having a surface contiguous with at least one recessed portion via a sidewall, the sidewall including an electrically-conductive and/or semi-conductive portion having a dimension substantially parallel to the raised portion of the substrate of less than 50 nanometers, wherein the surface of the raised portion is substantially non-electrically conductive and/or non-semi-conductive except for the electrically-conductive and/or semi-conductive portion of the sidewall;
wherein a non-conductive layer fills the recessed portion of the substrate; and
wherein the non-conductive layer is adapted and arranged to allow an electrical signal to pass through the non-conductive layer.

2. An article as in claim 1, further comprising a sample region to which the electrically-conductive and/or semi-conductive region is exposed and an electrical circuit, in electrical communication with the electrically-conductive and/or semi-conductive region, constructed and arranged to determine a change in an electrical property associated with the electrically-conductive and/or semi-conductive region responsive to an interaction of the electrically-conductive and/or semi-conductive region with a species in the sample region.

3. An article as in claim 1, wherein the electrically-conductive and/or semi-conductive portion of the sidewall has a thickness of less than about 40 nanometers.

4. An article as in claim 1, wherein the electrically-conductive and/or semi-conductive portion of the sidewall has a thickness of less than about 30 nanometers.

5. An article as in claim 1, wherein the substrate comprises an elastomer.

6. An article as in claim 1, wherein the substrate comprises poly(dimethylsiloxane).

7. An article as in claim 1, wherein the substrate comprises a patterning area comprising a plurality of raised and recessed portions over an area of greater than 1 cm$^2$.

8. An article as in claim 1, wherein the electrically-conductive or semi-conductive portion of the sidewall comprises at least two layers of material.

9. An article as in claim 1, comprising an electrically-conductive portion of the sidewall that comprises gold and titanium.

10. An article as in claim 1, wherein the substrate comprises a plurality of electrically-conductive or semi-conductive portions that are continuous with one another.

11. An article as in claim 1, wherein the substrate comprises a plurality of electrically-conductive or semi-conductive portions that are discontinuous with one another.

12. An article as in claim 1, wherein the sidewall comprises an electrically-conductive portion, and wherein the raised portion is substantially non-electrically conductive except for the electrically-conductive portion of the sidewall.

13. An article as in claim 1, wherein the sidewall comprises a semi-conductive portion, and wherein the raised portion is substantially non-electrically conductive except for the semi-conductive portion of the sidewall.

14. An article as in claim 1, comprising the non-conductive layer positioned over the electrically-conductive and/or semi-conductive portions.

15. An article as in claim 1, wherein the conformable polymeric substrate is substantially planar.

16. An article as in claim 1, comprising a microfluidic channel in communication with the substrate.

17. An article as in claim 16, wherein the microfluidic channel is in electrical communication with the electrically-conductive and/or semi-conductive portions of the substrate.

18. An article as in claim 1, wherein the conformable substrate is curved.

19. A sensor system, comprising:
an electrode comprising a conformable, polymeric substrate including at least one raised portion having a surface contiguous with at least one recessed portion via a sidewall, the sidewall including an electrically-conductive and/or semi-conductive portion, wherein the surface of the raised portion is substantially non-electrically conductive and/or non-semi-conductive except for the electrically-conductive and/or semi-conductive portion of the sidewall;
a sample region to which the electrode is exposed;
an electrical circuit, in electrical communication with the electrode, constructed and arranged to determine a change in an electrical property associated with the electrode responsive to an the interaction of the electrode with a species in the sample region;
wherein a non-conductive layer fills the recessed portion of the substrate; and
wherein the non-conductive layer is adapted and arranged to allow an electrical signal to pass through the non-conductive layer.

20. A system as in claim 19, comprising a chemical and/or biological substance positioned at the sample region and in electrical communication with the electrical circuit.

21. A system as in claim 20, wherein the biological substance comprises a cell.

22. A system as in claim 19, comprising a dielectric material positioned at the sample region and in electrical communication with the electrical circuit.

23. A system as in claim 19, comprising a non-conductive layer positioned over the electrically-conductive and/or semi-conductive portion.

24. A system as in claim 23, wherein the non-conductive layer fills the recessed portion of the substrate.

25. A system as in claim 23, wherein the non-conductive layer is adapted and arranged to allow an electrical signal to pass through the non-conductive layer.

26. A system as in claim 19, comprising a microfluidic channel in communication with the substrate.

27. A system as in claim 26, wherein the microfluidic channel is in electrical communication with the electrically-conductive and/or semi-conductive portion of the substrate.

28. A system as in claim 19, wherein the conformable substrate is curved.

29. A system as in claim 19, wherein the substrate comprises a plurality of electrically-conductive or semi-conductive portions that are discrete and individually addressable electronically.

* * * * *